United States Patent
Costantini et al.

[19]

[11] Patent Number: 6,113,473
[45] Date of Patent: Sep. 5, 2000

[54] METHOD AND APPARATUS FOR IMPROVED WIRE SAW SLURRY

[75] Inventors: Michael A. Costantini, Hudson; Jonathan A. Talbott, Amherst; Mohan Chandra, Merrimack, all of N.H.; Vishwanath Prasad, East Setauket, N.Y.; Allison Caster, Nashua, N.H.; Kedar P. Gupta, Merrimack, N.H.; Philippe Leyvraz, Nashua, N.H.

[73] Assignee: G.T. Equipment Technologies Inc., Nashua, N.H.

[21] Appl. No.: 09/065,769

[22] Filed: Apr. 24, 1998

Related U.S. Application Data

[60] Provisional application No. 60/044,937, Apr. 25, 1997.

[51] Int. Cl.[7] ................................ B24B 7/19; B24B 7/30
[52] U.S. Cl. .......................... 451/60; 451/446; 451/87; 451/88; 125/21
[58] Field of Search ...................... 210/806, 805, 210/96.1, 143, 195.1; 451/28, 87, 88, 99, 75, 5, 21, 6, 446, 60, 36; 209/3, 3.2, 4, 7, 9, 10, 208, 209, 210, 724, 725, 726, 17, 18, 269, 268; 125/21, 16.01, 16.02

[56] References Cited

U.S. PATENT DOCUMENTS 5,799,643  9/1998  Miyata et al. .................... 125/21
5,830,369  11/1998  Toyama ........................... 210/773

FOREIGN PATENT DOCUMENTS 9201819  8/1997  Japan .

*Primary Examiner*—Derris Holt Banks
*Attorney, Agent, or Firm*—Vernon C. Maine; Scott J. Asmus

[57] ABSTRACT

A slurry recycle process for use in free-abrasive machining operations such as for wire saws used in wafer slicing of ingots, where the used slurry is separated into kerf-rich and abrasive-rich components, and the abrasive-rich component is reconstituted into a makeup slurry. During the process, the average particle size of the makeup slurry is controlled by monitoring the condition of the kerf and abrasive components and making necessary adjustments to the separating force and dwell time of the separator apparatus. Related pre-separator and post separator treatments, and feedback of one or the other separator slurry output components for mixing with incoming used slurry and recirculation through the separator, provide further effectiveness and additional control points in the process. The kerf-rich component is eventually or continually removed; the abrasive-rich component is reconstituted into a makeup slurry with a controlled, average particle size such that the products of the free-abrasive machining method using the recycled slurry process of the invention are of consistent high quality with less TTV deviation from cycle to cycle for a prolonged period or series of machining operations.

19 Claims, 4 Drawing Sheets

METHOD AND APPARATUS FOR IMPROVED WIRE SAW SLURRY

This application relates to and claims priority to U.S. application Ser. No. 60/044937, filed Apr. 25, 1997.

This invention was made with Government support under Contract No. DE-FG02-95ER81978 awarded by the Department of Energy. The Government has certain rights in this invention.

BACKGROUND OF THE INVENTION

1. Technical Field of the Invention

The invention relates to the reclamation and reuse of the abrasive slurries used in free-abrasive machining operations; and more particularly to the reclamation and reuse of abrasive slurries used with wire saws in the cutting of wafers from ingots of silicon and various other materials.

2. Background Art

The process of wire slicing for the production of wafers from hard crystal uses an abrasive "slurry" to accomplish the cutting operation in a wire saw. The slurry is a suspension of abrasive particles in a liquid called a "vehicle" or "carrier", which is applied to the wire during the slicing operation. The abrasive slurry causes channels to be ground in the crystal, separating the crystal into slices called wafers. The wafers produced by this method are used to make electronic devices, photovoltaic devices, optical windows, and other applications requiring that they have a particular thickness, flatness, and surface smoothness. The term "wire slicing" is partly a misnomer, since the wire does not do the slicing, but acts to transport the abrasive slurry, which slices by the process called "free-abrasive machining."

Free-abrasive machining is the general name for a process by which abrasive particles are suspended in a fluid medium used to transport them to the surface of a workpiece, typically of hard material like crystal or ceramic, where the particles abrade the workpiece in such a way as to create a feature in the surface of the workpiece or to separate the workpiece into two or more pieces. It is distinguished from bonded-abrasive machining, where the abrasive particles are bonded to a solid object, which is used to deliver the abrasive to the surface of the workpiece. Examples of free-abrasive machining processes include wire-sawing, ultrasonic machining, water-jet cutting, and sandblasting.

A wire saw is comprised of a collection of wires oriented under tension by a mechanical device that allows them to be driven in the same direction at high-speed. A wire saw drives hundreds of these wires simultaneously in a formation known as a "web", upon which the abrasive slurry is continuously deposited for transport to the workpiece. The slurry acts to abrade the workpiece, to flush the abraded particles away, and to cool the workpiece. The slurry is held in a sump and pumped onto the web. It is allowed to flow off of the web through a drain to return to the sump for recirculation to the web. A mechanical device slowly forces the workpiece, or "ingot" through the web, subdividing it. This method allows for the production of large numbers of uniformly sliced wafers.

During the slicing process the abrasive slurry becomes contaminated with ground material ("kerf") from the crystal or other material being sliced or sawn. In grinding practice, fine particles from machining are called "swarf". The particles of kerf are finer than the particles of abrasive that produce it.

In general, the ingot can be any material of any dimension, so long as it can be cut, ground, machined, or otherwise shaped by abrasive action. The kerf can come from any abrading process that takes place using a free-abrasive machining technique where the abrading particle is suspended in a fluid as a slurry, and the abrading process generates a particulate material that is finer than the abrading particle. The abrading process can be done by wire slicing, ultrasonic machining, lapping, polishing, water-jet cutting, or other means.

Abrasive is a major cost of operation for the production of wafers from hard materials by free-abrasive machining. The disposal of used abrasive is both an expense and an environmental issue for plants that use the process. The ability to recover and re-use abrasive that has been contaminated represents a potential cost-savings and reduction of waste volume of the abrasive materials.

The abrasive slurry used in wire saws is critical to the success of the wafer slicing operation. The quality of the abrasive and its liquid suspending medium or carrier is closely controlled. Special grades of abrasive and carrier are manufactured and sold, at premium prices, specifically to improve and stabilize slicing operations. Abrasive grades specifically produced for wafer slicing on a wire saw are controlled to a narrow size distribution. ESK F500™ abrasive material, for example, has a specification for particle size of 12.8+/-1.0 microns. The quality of the abrasive slurry used in the wire saw has come to be recognized as a key factor in its successful operation. The slurry components are metered carefully to insure consistency, and the flow-rate, density, viscosity, and temperature of the slurry are carefully monitored and controlled before and during the slicing process. Shin-Etsu Handotai Company's patent disclosure EP0798091A2, for example, describes methods to control slurry viscosity in a wire saw by dilution with water to produce uniform thickness in sliced wafers.

As the slurry gradually becomes contaminated with kerf through use, the thickness specifications of the wafers produced during the cutting process under comparable production conditions change. Specifically, wafer thickness, total thickness variation (TTV), and standard deviation (SD) of TTV change as abrasive slurry is used to slice successive batches of wafers. TTV is defined as the difference between the minimum and maximum thickness measured.

The general trend is that the thickness of the wafers increases during each successive batch, while TTV typically declines slightly during the second batch, and then increases considerably in the third and fourth consecutive batches of wafers. This is considered typical behavior for new abrasive, and it is commonly accepted in the industry that the second batch is typically the highest quality as measured by TTV. It has been suggested that a small amount of fine particle contamination is responsible for this decrease in TTV after the first batch, and has lead to a not uncommon practice of retaining a small amount of exhausted slurry to be added to fresh slurry as a pre-conditioning step to lower the TTV of the first batch.

The standard deviation of TTV typically increases after the first batch and then rapidly in the third and again in the fourth batch if a fourth is done. An increase in standard deviation indicates increasing variation in wafer quality within the batch of wafers produced during the batch, which indicates that the process is displaying less statistical control. These measurement techniques and trends are well-understood in the industry, and the wafer-quality phenomena as described here are generally accepted as facts.

Thickness is measured at five points on the wafer. Four measurements are taken a small distance from the edge of the wafer around its periphery, and one at the center. The average thickness is the average of the five measurements. The TTV is determined by the difference between the largest and smallest of the five measurements.

The amount of cutting that a given abrasive batch can do at acceptable quality can be extended by slowing the cutting process. This extends the time required for wafer production and thus raises the cost of production. Therefore, when wafer quality decreases below standards at an acceptable production rate, the slurry is disposed of as waste. For typical photovoltaic applications, for example, abrasive slurry is used three to four times in succession without modification and then discarded.

Inventions for the recovery of abrasives in grinding and blasting operations are described in previous patents. Gritblasting operations in particular have patented processes for abrasive reclaim that include purification steps that provide a similar benefit to the abrasive by removing contamination from the abrasive. These inventions are typically pneumatic in nature, are not intended for wafer slicing, and can not be applied in the context of our invention.

A Varian Associates report, *Slicing of Silicon into Sheet Material, Final Report*, by J. R. Fleming et al, Sep. 21, 1979, studied wafer slicing with a gang saw (reciprocating blades) from 1976 to 1979 with cost reduction as the objective, and discussed abrasive lifetime and abrasive contamination during the slicing of wafers with a gang saw (reciprocating blades), and the possibility of recovery and purification of the abrasive in the slurry.

The authors attempted filtration and cycionic methods of abrasive recovery, but expressly declared they "did not work". They successfully recovered a portion of dry abrasive in a solid-bowl centrifuge. They also employed metal removal techniques and removed additional kerf material by solvent washing. The abrasive yield was 30% of the initial amount, although the authors predicted a higher percentage was achievable.

New abrasive was mixed with the recovered abrasive at a 2/1 ratio and used to prepare a new batch of slurry which was used successfully for another test cutting of wafers. The report concludes that multiple recoveries and recombining of used abrasive with new abrasive at the same ratio for use in slurries should have no detrimental effects on cutting time or wafer thickness, while achieving desired cost reductions.

The emphasis of this work was on cost reduction through the recovery and re combination of such amount of the used abrasive material as will not negatively impact production time or wafer thickness. Other approaches to the freeabrasive machining process and the recycling of used slurry, with other potential benefits, have apparently been obscured by the tight focus on cost reduction through recovery of abrasive material of this and similar efforts.

SUMMARY OF THE INVENTION

The invention in its simplest form is a slurry recycle process for use in free-abrasive machining operations such as for wire saws used in wafer slicing of ingots, where the used slurry is separated into kerf-rich and abrasive-rich components, and the abrasive-rich component is reconstituted into a makeup slurry. During the process, the average particle size of the makeup slurry is controlled by monitoring the condition of the kerf and abrasive components and making necessary adjustments to the separating force and dwell time of the separator apparatus. Related pre-separator and post separator treatments, and feedback of one or the other separator slurry output components for mixing with incoming used slurry and recirculation through the separator, provide further effectiveness and additional control points in the process. The kerf-rich component is eventually or continually removed; the abrasive-rich component is reconstituted into a makeup slurry with an optimal, average particle size such that the products of the freeabrasive machining method using this recycled slurry process are of consistent high quality with less TTV deviation from cycle to cycle for a prolonged period or series of operations as compared to other recycle or non-recycle processes.

There are several steps, which can vary in detail depending on the particular application of the process. The basic steps are: 1) removal and pre-treatment of the spent slurry from the free-abrasive machine tool to the slurry recycling system; 2) controlled processing of the slurry through a separator apparatus to segregate the slurry into two components, one containing the larger, heavier, abrasive particles and the other containing the smaller, lighter, kerf particles; 3) dilution and other post-separator treatment of the recovered abrasive component to achieve the proper concentration and other properties for reuse as a makeup slurry; 4) return of the reconstituted abrasive slurry to the machine tool. The process can be operated as a batch or continuous operation, manually or by a computer control system, as needed to suit plant practice or to accommodate the design and capability of a particular separator apparatus.

Demonstrative of the effects of the new process, recycled abrasive slurry from a centrifuge recovery system configured and operated in accordance with the process of the invention was used to slice wafers with a wire saw, using the same conditions as described in the prior art example of the background section.

Table 1 shows the effects of three successive batches of wafers on the same slurry on a commerical wire saw. The average particle size decreases during each successive batch as measure on a Coulter LS100 particle analyzer using the Fraunhofer optical model. The slurry was new at the start of the first batch and did not undergo recycling or modification of any kind between successive batches of wafers.

After the third batch the slurry was discarded in each case. In this example a "batch" is defined as slicing two 500-mm long silicon crystal slabs (ingots) into wafers of 320 microns nominal thickness. In practice the ingots may be longer or shorter, have a square, round, oblong or other cross-section, and be sliced into wafers that are thicker or thinner, or the result can be some other geometry besides that of a wafer.

The wafer data in Table 1 is taken over a series of 20 batches of wafers. All values in Table 1 are in microns. Table 1 shows that the average TTV of the wafers decreases 2.3 microns from the first batch to the second batch, and increases 2.5 microns from the second batch to the third batch. The average thickness of the wafers is also shown to increase with each successive batch. As described in the background of the invention, this is typical of wire sawn wafer quality behavior.

TABLE 1

| Successive batches of wafers on Slurry | Median Particle Size | Average TTV | SD of TTV | Average Thickness |
| --- | --- | --- | --- | --- |
| 0 | 12.66 | — | — | — |
| 1 | 9.38 | 17.8 | 9.8 | 318 |

TABLE 1-continued

| Successive batches of wafers on Slurry | Median Particle Size | Average TTV | SD of TTV | Average Thickness |
| --- | --- | --- | --- | --- |
| 2 | 5.67 | 15.5 | 10.2 | 319.8 |
| 3 | 3.82 | 18 | 23 | 322.7 |

TABLE 2

| Successive batches of wafers on Slurry | Median Particle Size | Average TTV | Average SD of TTV | Thickness |
| --- | --- | --- | --- | --- |
| 0 | 9.42 | — | — | — |
| 1 | 7.17 | 11.3 | 6.7 | 321 |
| 2 | 3.28 | 12.4 | 9.8 | 324 |
| 3 | 3.13 | 12.2 | 21.4 | 322 |

Referring now to Table 2, data from 10 batches of wafers using recycled abrasive slurry were used to generate the data in Table 2, which lists the particle size of the abrasive after recovery and after each subsequent batch. All values in Table 2 are in microns. Prior to slicing the wafer Table 2, the slurry had previously been made from new abrasive and used to slice wafer in the same process as that which produced the wafers in Table 1, had been exhausted by undergoing consecutive batches of wafers, and had then been treated by recycling in the process as described here.

The size of the recovered abrasive as shown before cutting was similar to that of the new abrasive in Table 1 after one batch. The average particle size of the abrasive decreases with sucessive batch, as was the case in Table 1. However, the magnitude of the difference in median particle size between the new and "exhausted" abrasive in Table 1 is 3.24 microns greater than the difference between the recycled and subsequently exhausted abrasive in Table 2.

The TTV of wafers produced by the recycled slurry is consistently lower than that of the wafers produced using new abrasive slurry. Further, the TTV data no longer shows a decrease of 2.3 microns from batch 1 to batch 2 and an increase of 2.5 microns from batch 2 to batch 3, as was the case in with new abrasive slurry. Rather, the TTV of each of the three consecutive batches of wafers are within approximately one micron of one another. Overall, recycled abrasive slurry produced wafers that are lowers that are lower in TTV on average than those produced by new abrasive slurry.

Further, recycled abrasive slurry produced wafers having a lower overall standard deviation of TTV for a corresponding batch than wafers produced using new slurry. The standard deviation of TTV in Table 2 is between 0.3 and 3.1 microns lower for each batch using recycled slurry compared to new slurry having undergone the same number of consecutive batches of wafers.

The average thickness of wafers produced using the recycled slurry is 3 microns thicker for batch 1, 4.2 microns thicker for batch 2, and 0.7 microns thinner for batch 3 than for new slurry. Overall, recycled slurry produced wafers that are thicker on average than those produced in Table 1 by new slurry. Furthermore, the trend for new slurry of increasing thickness of wafers from successive batches of wafers on the same slurry is eliminated by using recycled slurry, producing wafers in Table 2 which are closer in thickness between consecutive batches of wafers than from new abrasive in Table 1.

It is clear from Table 1 and Table 2 that the particle size distribution of the slurry, expressed as the median particle size, has a direct effect on the thickness and TTV of the wafers. It is also clear that controlling the particle size distribution of the slurry by slicing with slurry treated by prior slicing and recycling as described here, such that the change in median particle size from the start of the first batch to the end of the third batch is smaller in the case of the recycled slurry compared to the new slurry, will produce wafers on a wire saw that are on the average thicker, lower in TTV, and more consistent in thickness and TTV from batch to batch than would be the case had the abrasive not undergone such recycling treatment.

Referring now to Table 3, below. Table 3 illustrates the average and standard deviation of the data of Tables 1 and Table 2. All values in Table 3 are in microns. Table 3 illustrates that treatment of the slurry by the recycling process results in a reduction in the average and standard deviation of the median slurry particle size compared to slurry which had not been treated. The effect of the said reductions is a corresponding reduction in the average and the standard deviation of TTV and of average thickness of the wafers produced using the treated, recycled slurry, compared to the wafers that were produced using slurry which had not previously undergone treatment by the recycling process.

TABLE 3

| batches of wafers on slurry | Particle size with treatment | Comparative Example: Particle size with no treatment | TTV with treatment | Comparative example: TTV with no treatment | Average Thickness with Treatment | Comparative example: Average Thickness with no Treatment' |
| --- | --- | --- | --- | --- | --- | --- |
| 1 | 7.17 | 9.38 | 11.3 | 17.8 | 321 | 318 |
| 2 | 3.28 | 5.67 | 12.4 | 15.5 | 324 | 319.8 |
| 3 | 3.13 | 3.82 | 12.2 | 18 | 322 | 322.7 |
| Average | 4.53 | 6.29 | 12.0 | 17.1 | 322 | 320.2 |
| Std. Dev. | 2.29 | 2.83 | 0.59 | 1.39 | 1.53 | 2.37 |

The wafer lots produced by the treated, recycled slurry had no additional wafers rejected due to breakage, cracking, or other defects which would ordinarily cause wafers to be rejected, in comparison to wafers which had been produced using slurry which had not been previously undergone treatment by the recycling process.

Still other objects and advantages of the present invention will become readily apparent to those skilled in this art from the following detailed description, wherein we have shown and described only a preferred embodiment of the invention, simply by way of illustration of the best mode contemplated by us on carrying out the invention. As will be realized, the invention is capable of other and different embodiments, and its several details are capable of modifications in various obvious respects, all without departing from the invention.

DESCRIPTION OF THE PREFERRED EMBODIMENT

For the purpose of this disclosure, the block diagrams of the drawings are used to describe preferred embodiments only. The drawings use rectangular figures to indicate principal apparatus components of some sort and circular figures to indicate principal process steps of some sort. The process steps of the circular figures may be implemented by commonly known means and structures independent of or in association with the illustrated principal apparatus components. The use of specifically identified apparatus components is not intended to be a necessary limitation to the scope of the invention, but rather a useful way to describe a specific function or functions of the overall process which could be likewise implemented by alternative apparatus components.

Figure 1:
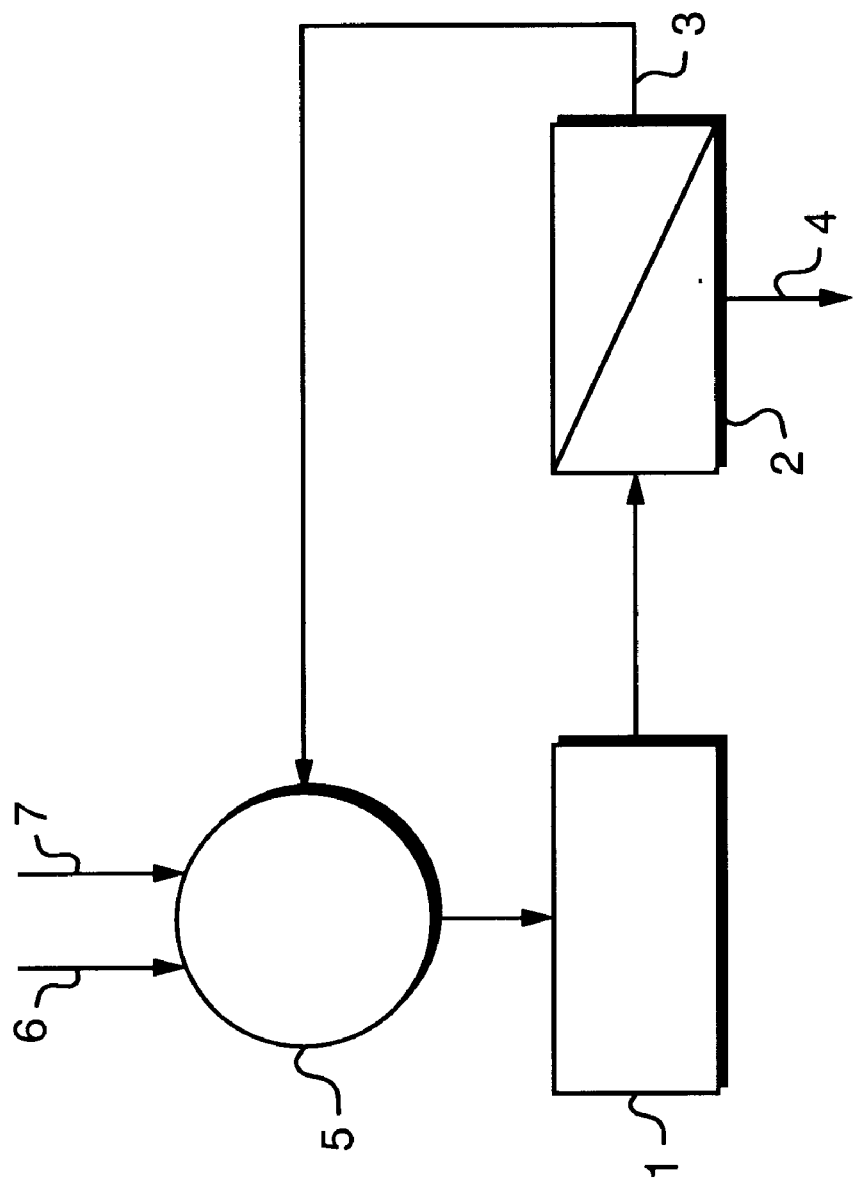
FIG. 1 is a simplified block diagram flow chart of a wire saw and particle separator used to separate out a finer particle component of spent wire saw slurry and recycle the remainder to the saw.

Referring to FIG. 1 as a reference point from which to launch the description of the preferred embodiment, a simple dry abrasive recycle system that might be inferred from the prior art, is illustrated with a block diagram flow chart as a wire saw (1), where spent slurry is transferred into separator (2), which recovers a dry batch of abrasive material (3), and a kerf-rich spent slurry waste product (4), which is removed from the process. Dry abrasive material (3) is then recombined at process step (5) with new abrasive material (6) and new carrier (7) to create makeup slurry for return to wire saw (1).

Figure 2:
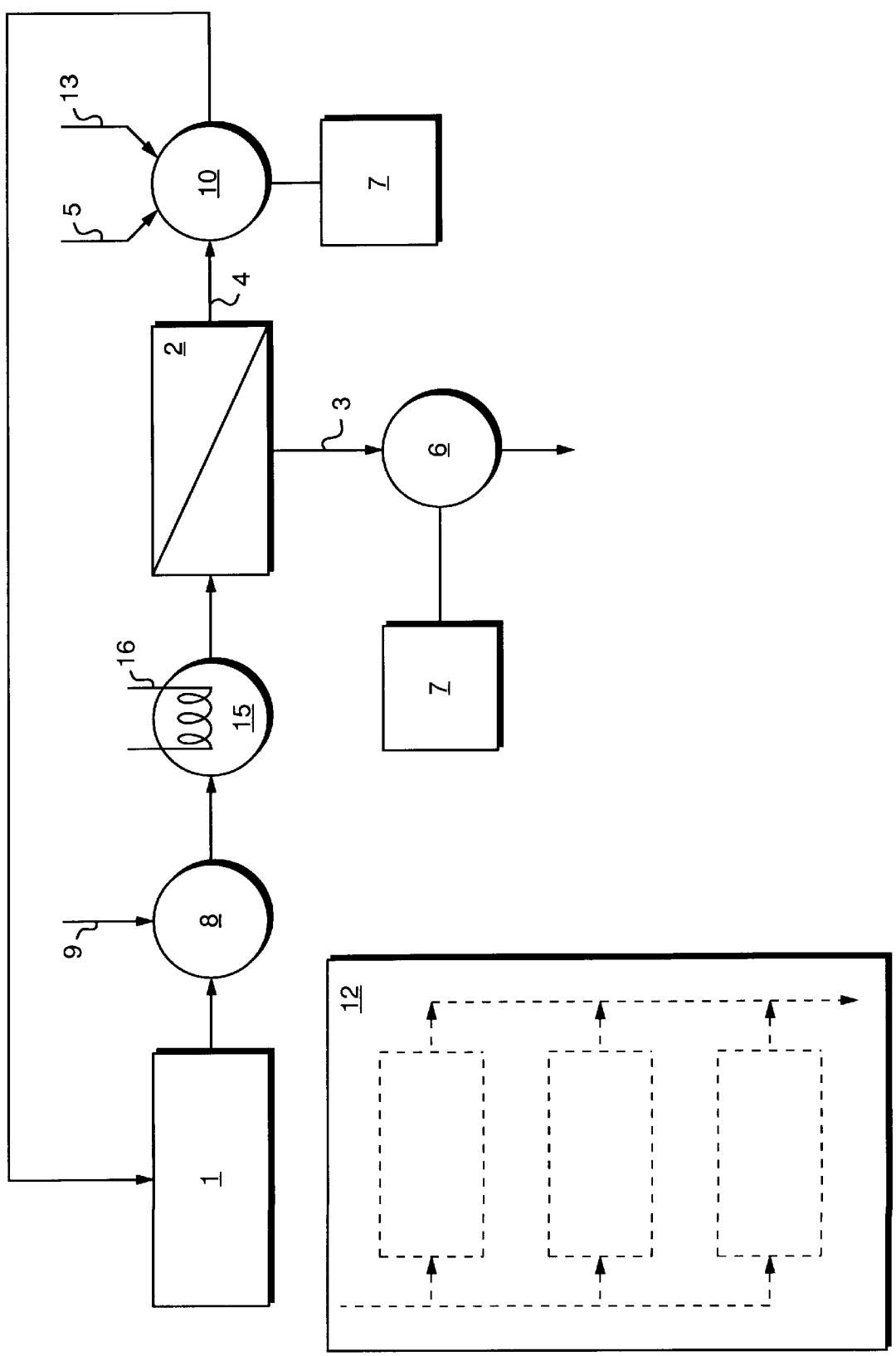
FIG. 2 is a simplified block diagram flow chart of the wire saw slurry recycle process with a wire saw, a separator section, pre-separation treatment of slurry, and post separation treatment of the larger particle slurry component.

Now referring to FIG. 2, a block diagram flow chart showing an embodiment of the invention for continuous, controlled processing of spent slurry, an abrasive slurry is used in wire saw (1) where it becomes contaminated with saw kerf from the ingot being sawn. The spent slurry is transferred either manually, or by gravity, pump or other means into separator (2), typically a centrifuge or a wet cyclone, where the slurry is separated into a large particle, abrasive-rich slurry component (4), and a smaller particle, kerf-rich slurry component (3).

Prior to transferring the slurry to the separator(2), the slurry may optionally be subjected to pre-treatment process step (8) with a suitable fluid or surfactant (9), compatible with the carrier of the slurry, to facilitate processing in separator (2). In addition to, or in place of the pre-treatment step (8), the slurry may be subjected to temperature control process step (15), by adding heat (16), to lower the viscosity of the carrier to enhance separation characteristics of the slurry. The pre-treatment process step (8) and temperature control process step (15) are accomplished in a separate vessel (not shown), or alternately, in-situ during the transfer of the slurry from saw (1) to separator (2).

The concentration of particles in the slurry is determined by measuring specific gravity and equating it to the corresponding concentration for the materials of the slurry. Process step (6) uses hydrometer (7) to measure the specific gravity of kerf-rich slurry component (3). This concentration measurement may also be done by a vibrating reed densitometer, coriolis meter, by weighing a measured volume, or other comparable means. The specific gravity is measured in situ or by removing and testing a sample. If the specific gravity of the kerf-rich component (3) is above the target limit, the process is modified either by increasing the separating force or increasing the residence or dwell time of the slurry in separator (2). Conversely, if the specific gravity of the kerf-rich slurry component is below target, the process is modified by decreasing the separating force on the slurry and/or decreasing the residence or dwell time in the separator.

The monitoring of specific gravity or other characteristics indicative of particle concentration, and adjustment of separator force, dwell time, and related operational settings, and other or all feedback and control functions of the invention for this and other embodiments, may be configured to be manually executed, or automated by the use of a computer control system, not shown here, with a program that receives specific gravity and other sensory input data, and transmits control signals to the separator and other appropriate transducers throughout the system of the invention. The hardware components for an automated control system are readily available commercially. The computer program embodies the process of the invention, with variations specific to the particular application. Computer control of the recycle process may be integrated with control of the free-abrasive machining process for greater automation benefits.

Still referring to FIG. 2, after process step (6), the kerf-rich slurry component (3) is removed for disposal or further processing for related or other purposes, such as recovering the carrier fluid or kerf material, or further analysis for trace materials or contaminants such as iron particles from the saw wire. The abrasive-rich slurry component (4) may be at a higher or lower concentration of abrasive than desired for optimum re-use. The concentration is determined by measuring its specific gravity at process step (10) with another hydrometer (7), as in process step (6). If concentration adjustment is necessary, additional abrasive material (13) or carrier material (5) is added to slurry component (4) until the specific gravity is at the proper value for re-use, at which point it is returned to wire saw (1).

The embodiment of FIG. 2 can serve wire saw (1), as shown, or alternatively can be connected and controlled to serve a plurality of wire saws (12) or other free-abrasive machine tools, each transferring spent slurry independently into the slurry reclamation system and admitting the rejuvenated or makeup slurry as needed.

The following data illustrates a specific example of this embodiment in practice: 508 lb. of SiC slurry having a density of 1.68 kg/l was produced for recovery and decontamination after slicing 4 batches of two silicon ingot each, for a total of 8 ingots sliced. The slurry is considered fully exhausted under these conditions. The slurry had originally been prepared from virgin materials; no portion of the slurry or its components had previously been treated for recovery.

The slurry was pumped into the recovery system, which used a decanter centrifuge as the separator. The speed of the centrifuge and the feed pump were adjusted until the density of the kerf-rich phase read 1.315 kg/l at 80 degrees F. using a standard laboratory hydrometer. After each adjustment of centrifuge speed, the centrifuge conveyer was adjusted to maintain a constant solids content in the abrasive-rich phase.

Total process time for the recovery operation was 1 hour and 23 minutes. A total of 227 pounds of abrasive rich phase and 281 pounds of kerf-rich phase were collected. To achieve suitable makeup slurry, the abrasive rich phase was diluted with carrier fluid until its density reached 1.58 kg/l, after which the total weight of the abrasive rich-phase was 287 pounds. The recovery of abrasive rich phase was therefore 56%.

The makeup slurry was used again in the wire saw. The production yield of silicon wafers sliced with the recovered abrasive was 99%. The particle size analysis for each of the phases shows that the exhausted SiC had a median size 49% of the size of virgin SiC, that the recovered abrasive had a particle size 99% of the size of the virgin SiC, and that the particle size of the kerf-rich phase was 12% of the size of the virgin SiC.

The particle size results of the above example are as follows:

| Sample | Phase | Mean Size (um) | Mean Size as a % of Virgin SiC |
| --- | --- | --- | --- |
| F500-S | Virgin SiC | 12.66 | 100 |
| s057a4 | Exhausted | 6.23 | 49 |
| Cake 8 | Abrasive-Rich | 12.48 | 99 |
| Centrate | Kerf-Rich | 1.47 | 12 |

Figure 3:
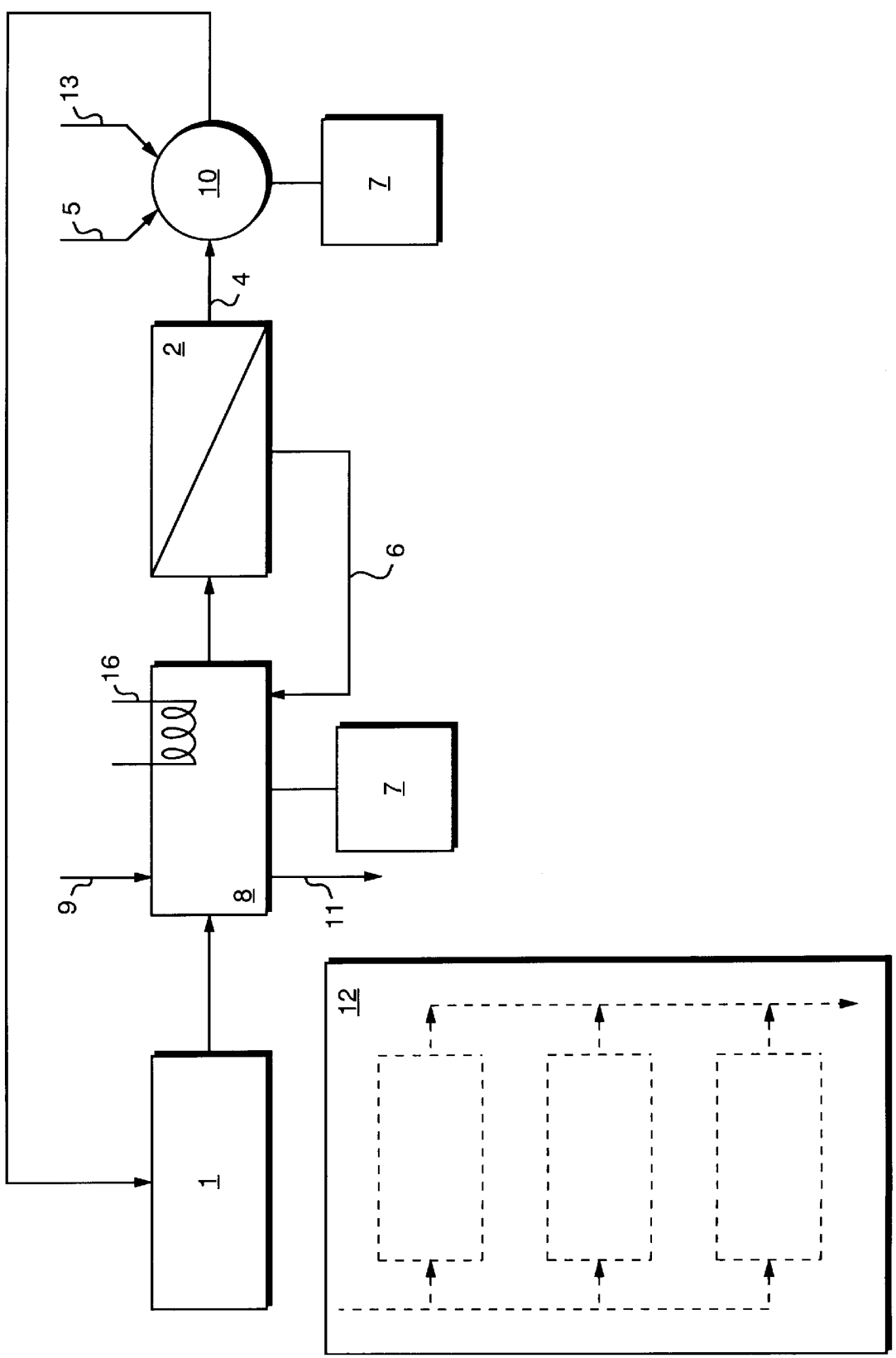
FIG. 3 is a simplified block diagram flow chart of the wire saw slurry recycle process with a wire saw, a pre-separation vessel for treating slurry, a separator section, return of the smaller particle slurry component to the pre-separation vessel, and post-separation treatment of the larger particle slurry component.

Referring now to FIG. 3, there is illustrated another embodiment of the invention with an abrasive slurry used in wire saw (1) where it becomes contaminated with kerf. Suitable piping connects wire saw (1) for batch transfers to vessel (8) of the slurry recycle system. In vessel (8), the slurry may optionally be subjected to pre-treatment with a suitable fluid, surfactant (9), compatible with the carrier of the subject slurry, to better facilitate processing in the separator. In addition to, or in place of pre-treatment with fluid (9), the slurry may be subjected to temperature control by adding or removing heat (16), to control the separation characteristics of the slurry, to increase yield or quality, or to generally facilitate the overall process.

The treated slurry is pumped from vessel (8) into separator (2), where the slurry is separated into larger particle, abrasive-rich slurry component (4), which is pumped forward for further processing and re-use, and smaller particle, kerf-rich slurry component (6), which is is recycled back into vessel (8).

The specific gravity of the contents of vessel (8) is measured using hydrometer (7), or a vibrating reed densitometer, coriolis meter, or by weighing a measured volume, or by other comparable means. As long as the specific gravity is above the target, the circular flow of slurry continues between vessel (8) and separator (2). When the specific gravity in vessel (8) falls below target, the circular flow is stopped, and the contents of vessel (8) are removed as waste product (11). Waste product (11) may, of course, be further processed for recovery of carrier fluid or kerf material, or analysis of trace components such as iron particles or other contaminants.

Slurry component (4) may be at a higher or lower concentration of abrasive than desired for optimum re-use. The specific gravity is measured at process step (10) with another hydrometer (7) or with other comparable means. If concentration adjustment is desired, abrasive material (13) or carrier material (5) is added as needed to the abrasive-rich slurry component (4) until the specific gravity is at the proper value for re-use, at which point it is ready for return to the wire saw (1) for re-use.

Alternatively, the system of the invention can service a plurality of wire saws (12), each transferring spent slurry independently to the system and being recharged as or when refreshed slurry is available.

The following data illustrates a specific example of this embodiment in practice: 507 lb. of SiC slurry having a density of 1.653 kg/l was produced for recovery and decontamination after slicing 2 batches of two silicon ingot each, for a total of 4 ingots sliced. The slurry is considered fully exhausted under these conditions. The slurry had originally been prepared from abrasive recovered by the same method, so that it is considered exhausted after slicing only 4 ingots.

The slurry was pumped into the recovery system, which used a decanter centrifuge as the separator. The speed of the centrifuge, conveyer, and the feed pump were pre-set to achieve a consistent solids content in the abrasive-rich phase. The density of the kerf-rich phase was measured using a standard laboratory hydrometer until the reading reached 1.270 kg/l at 80 degrees Fahrenheit.

Total process time for the recovery operation was 2 hours. A total of 278 pounds of abrasive rich phase and 229 pounds of kerf-rich phase were collected. The abrasive rich phase was diluted with carrier fluid until the makeup slurry reached a density of 1.58 kg/l, after which the total weight of the makeup slurry was 360 pounds. The recovery of abrasive rich phase was therefore 71%.

The slurry was used again in the wire saw. The production yield of silicon wafers sliced with the recovered abrasive was 98%. The particle size analysis for each of the phases shows that the exhausted SiC had a median size 59% of the size of virgin SiC, that the recovered abrasive had a particle size 87% of the size of the virgin SiC, a nd that the particle size of the kerf-rich phase was 18% of the size of the virgin SiC.

The particle size results of the test are as follows:

| Sample | Phase | Mean Size (um) | Mean Size as a % of Virgin SiC |
| --- | --- | --- | --- |
| F500-S | Virgin SiC | 12.66 | 100 |
| 98030601 | Exhausted | 7.42 | 59 |
| 98030603 | Abrasive-Rich | 10.97 | 87 |
| 98030602 | Kerf-Rich | 2.29 | 18 |

Figure 4:
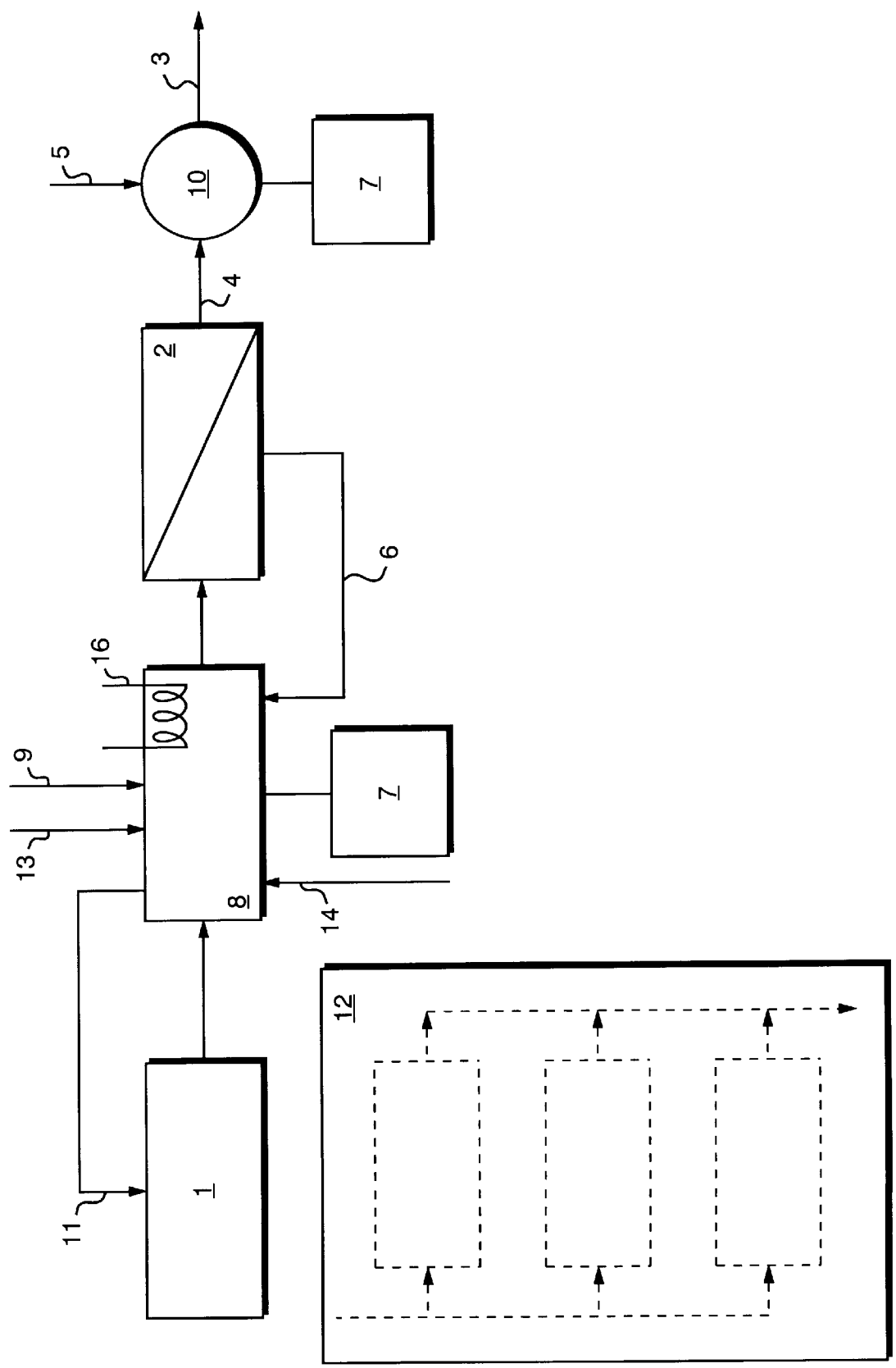
FIG. 4 is a simplified block diagram flow chart of the wire saw slurry recycle process with a wire saw, a pre-separation vessel for treating slurry, a separator section, recirculation of the larger particle slurry component to the pre-separation vessel, and return of processed slurry from the pre-separation vessel to the wire saw.

Referring now to FIG. 4, a block diagram flow chart for a second embodiment of the invention for batch operation is illustrated. Abrasive slurry is used in wire saw (1) where it becomes contaminated. The spent or contaminated slurry is batch transferred into the system of the invention, directly into vessel (8). Similar to the embodiment of FIG. 3, in vessel (8) the slurry may be subjected to pre-treatment with a suitable fluid or surfactant (9), compatible with the carrier of the subject slurry, to better facilitate processing in separator (2). In addition to or in place of the pre-treatment, the slurry can be subjected to temperature adjustment by adding or removing heat (16), to control the separation characteristics of the slurry, to increase yield or quality, or to generally improve the overall process consistency.

The slurry flows through suitable piping from vessel (8) into separator (2), where the slurry is separated into a smaller particle, kerf-rich slurry component (4), which is eventually removed from the system as waste product (3), and a larger particle, abrasive-rich slurry component (6), which is returned to vessel (8) for continuous reprocessing until the operation is complete.

The specific gravity of slurry component (4) is measured at process step (10) using a hydrometer (7), or by other comparable means. Process step (10) may be the monitoring of the solids concentration of the kerf-rich component (4) with an instrument such as a turbidimeter or other comparable means in lieu of hydrometer (7), by detecting its optical clarity or degree of light transmission through the fluid. If the specific gravity or optical clarity of the kerf-rich component (4) indicates the concentration is above the target level, the process is continued. If it is at or below target levels of concentration, the operation is complete.

While the process continues, the depletion of the liquid portion of the slurry in the vessel (8)/separator (2) loop, by the removal of the kerf-rich slurry component (4) from separator (2), is balanced by the controlled input of carrier liquid (13) into vessel (8) to keep the level of liquid in is the vessel relatively constant. The input of liquid (13) facilitates the extended removal of kerf-rich slurry component (4), allowing for the production of an abrasive-rich slurry component (6) that is lower in contamination than is typically achieved in the embodiment of FIG. 3.

The recycled slurry in the recirculating loop of vessel (8) and separator (2) may be at a higher or lower concentration of abrasives than desired for optimum re-use after the separation process has stopped, as is indicated in vessel (8) by hydrometer (7). If concentration adjustment is necessary, abrasive material (14) or liquid material (13) is added to the slurry until the specific gravity indicates the abrasives concentration is at the proper value for re-use, at which time the renewed slurry (11) is ready for recharging wire saw (1).

The following data illustrates a specific example of this embodiment in practice: A0.5" nominal diameter hydrocyclone was used as the separator (2) arranged as in FIG. 4 to recover and decontaminate the SiC abrasive from slurry used in a wire saw to slice 150 mm diameter by 400 mm long monocrystalline silicon ingots for semiconductor application.

Five gallons of used slurry containing 15 kg. SiC, having a mean particle size of 15.8 microns before slicing, was pumped from the slurry tank of the wire saw into the vessel (8). The slurry in this case is made from a suspension of SiC in a water-soluble carrier, and was further diluted with 27 gallons of water before being pumped into the hydrocyclone. The slurry was kept in a batch tank and a relatively coarse particle size underflow containing the abrasive-rich phase was recycled from the discharge of the hydrocyclone back to the batch tank.

The pressure in the hydrocyclone was kept at 45 psi by regulating the pumping speed from the vessel (8) and monitoring the pressure using a pressure gauge. A variable-speed electric drive was used to vary the speed of the feed pump by changing the frequency of the current fed to the motor, which drives the pump.

It is preferred to automate the pressure control of the hydrocyclone by adding a computer or PC-based controller, which receives a signal from a pressure transducer, located just before the inlet of the hydrocyclone, and adjusts the frequency output of the variable-speed drive accordingly.

A fluid level control valve supplies water to the tank via a normal water supply source or tap, which compensates for the depletion of the water through the cyclone overflow to keep the level constant so that the volume of the tank remains filled to 32 gallons.

By returning the abrasive-rich component to the tank and continuously ejecting the kerf-rich overflow, the abrasives are cleaned of contamination by the kerf to the desired level. After 210 minutes the overflow was clear, the pump was stopped and the suspended abrasive was allowed to settle. The preferred method to monitor the solids content of the overflow is by a suitable instrument such as a densitometer or a turbidimeter to determine a consistent solids concentration in the overflow at which to terminate the operation.

The recovered abrasive was oven-dried to determine its weight. Total recovery was 6 kg. Yield was 40% dry-basis. Samples of slurry from the vessel(8) were taken at intervals during the process to determine the change in particle-size distribution of the recovered abrasive-rich component. The particle size distribution increases with time as follows:

| Time (minutes) | Median Particle Size (microns) |
| --- | --- |
| 0 | 14.99 |
| 30 | 15.29 |
| 60 | 15.95 |
| 120 | 16.49 |
| 210 | 16.40 |

This result demonstrates that the recycling arrangement in FIG. 4 is capable of removing surplus contamination attributed to fine particles, and is capable of controlling the median particle size of the slurry at an optimum size, expanding the quality control capabilities of the arrangements shown in FIGS. 2 and 3.

The invention is capable of other than the various embodiments illustrated and described above. For example, the separator can be replaced or augmented by any of several devices suitable for separating fine particle in suspension, by size, including in particular, a decanter centrifuge and a hydrocyclone. Both of these devices work to separate the particles into coarse and fine fractions by enhancing the differences in their settling rates, but vary considerably in one or more ways.

In the case of a decanter centrifuge, the separator is arranged as a spinning horizontal cylinder that is tapered to a cone end, contains an annular weir to set the liquid height at the opposite end, and contains an internal rotating auger to force captured solids out of the tapered end. Feed slurry is continuously pumped into the center of the cylinder. The separator forces solid particles out of suspension and concentrates them with the centrifugal force created by its spinning action. Larger particles tend to separate first and sediment at an elevated concentration, while finer particles tend to remain suspended in the liquid phase at a reduced concentration than that of the feed.

In the case of exhausted wire saw slurry, the finer particles are predominantly kerf-and iron contamination, whereas the larger particles are predominantly abrasive. The liquid phase is therefore more iron and kerf-rich than the exhausted slurry and discharges from the large end of the cylinder, while the concentrated sediment is more abrasive rich than the exhausted slurry and discharges as a thick paste from the tapered-end of the cylinder.

This type of continuous centrifuge is well-suited to the task because it is capable of recycling abrasive from a typical slurry used in a wire saw, having a high (50%+wt.) solids content and an elevated (100–500 centipoise) room-temperature viscosity, without dilution, yet it facilitates continuous discharge of the abrasive-rich phase at 80%+wt. solids, thus eliminating the manual unloading required by batch centrifuges. This capability is due to the fact that it is driven up to several thousand RPM by an external motor, allowing it to develop a centrifugal force several thousand times that of gravity.

In contrast, the design of the hydrocyclone requires that the slurry be diluted to about 25% solids or lower with water or other low-viscosity liquid to facilitate the separation, and this practice is well-known as a matter of historical application for separators of this type. Since the cyclone contains no moving parts, and relies on external fluid pressure to generate the centrifugal forces required to make a separation, the maximum centrifugal force generated by the cyclone is much less than that of a decanter centrifuge.

To operate a hydrocyclone in the particle size range below 20 microns, with which we are concerned, the solids content of the slurry needs to be reduced through this dilution step. The reduction in solids content and fluid viscosity increases the terminal velocity of particles in the cyclone, and therefore permits the cyclone to make the required separation even at the reduced centrifugal force that the cyclone produces. The cyclone in this case discharges a concentrated abrasive-rich phase typically called "underflow", and a less-concentrated kerf-rich phase typically called "overflow".

The abrasive-rich phase in this case is more likely to be recovered at or below the solids content required by the wire saw, depending on the particular separation efficiency required to produce adequate quality of recycled abrasive, and so is less likely to require dilution for return to the slicing process as in the case of the decanter centrifuge, but more likely to require the addition of abrasive to increase its solids content.

The recycling process reduces not only the kerf-content of the abrasive slurry, but it also reduces the iron contamination present in the slurry caused by abrasion of the wire used in the wire saw. Elevated iron levels can effect the slicing process by making the slurry more conductive, leading to false shutdown alarms due to ground faults indicative of broken wire. It is critical to keep iron levels low in order to maintain a reliable wire saw operation using recycled abrasive. In the following example, during four separate runs, iron levels in the slurry were shown to maintain controllable levels by normal application of the recycling process.

The recycling process was operated as indicated in FIG. 2 and the results recorded for 60 cycles. In each case, the wire saw was operated per normal procedures common in the art. The ingot sliced in this case was pure single-crystal quartz, which is known to be extremely low in contamination and for all practical purposes contains no iron. The slurry used to slice the quartz was F600-WS™ SiC abrasive from Electro-Abrasives Co., and is produced according to FEPA standards for high-quality abrasive. Abrasive of the type and grade used in wafer slicing on a wire saw is very pure, and typically contains less than 0.04% (percent) iron by weight.

Through inductively coupled plasma (ICP) analysis, iron levels were shown to increase from a typical starting value for fresh slurry of 0.004% by weight to an average of 0.83% by weight based on total slurry. The ICP results show that the recycled abrasive contains an average of 0.36% by weight iron, while the kerf-rich phase shows elevated iron levels of 1.17% by weight on average.

This example demonstrates that the iron contamination is at a particle size that is on the average at least as fine or finer than the average particle of kerf-contamination, and that the recycling process is removing an average of at least 50% by weight of iron from the abrasive-rich phase and concentrating it into the kerf-rich phase.

The invention is susceptible to various embodiments. For example, a free-abrasive machining slurry recycle system for processing used slurry into makeup slurry of constant average particle size may consist of a pre-separator section where used slurry from a free-abrasive machine tool is received and conditioned for further processing in a separator where the slurry is reduced into an abrasive-rich component and a kerf-rich component. The abrasive-rich component output will contain relatively larger heavier particles and the kerf-rich component output will contain relatively smaller lighter particles as compared to the total mixture entering the separator.

The system would have sensors for monitoring particle concentration and other variables of one or the other or both components, and be adjustable for setting the separating force and dwell time of the separator in response to changes in these variables. The system would include the necessary connections and controls for adding additional abrasive or carrier to said abrasive-rich component as required in response to changes in particle concentration. The result of these adjustments to the separator and additions to the abrasive-rich component is the output of the system, the makeup slurry for recycling to the wire saw.

The system would also include connections and controls for dispensing the makeup slurry to the free-abrasive machine tool, and for removing the kerf-rich component from the system.

As a further example, such a slurry recycle system may be configured for operating in a batch mode where a free-abrasive machine tool is fully discharged of used slurry into a pre-separator section, and be subsequently recharged with makeup slurry from the recycle system. Alternatively, the system may be configured for operating in a continuous flow mode where the free-abrasive machine tool is continuously discharging used slurry into the pre-separator section, and is continuously being recharged with makeup slurry from the dispensing section. The system may be further configured for continuous or controlled recirculation of one or the other slurry component from the separator to the pre-separator section for mixing with additional spent slurry and reflow through the separator, in response to changes in particle concentration.

As a yet further example, the separator of such a recycle system may be a centrifuge, a wet cyclone, or other device suitable for discriminating particles of this size range in suspension. There may be multiple separators or separation stages connected in parallel or series, each with or without a recirculation loop, to provide additional stages of separation to obtain the optimal discrimination and control of particle size and type going into the makeup slurry.

As a still yet further example, a recycle system of he invention may be configured with a computer control system for receiving inputs from various sensors monitoring particle concentration and other variable, and for sending control signals for causing corresponding adjustments to the separator and to the other sections where pre or post separator treatments are applied or abrasive or carrier material added.

As an additional example, the invention can be characterized as a free-abrasive machining slurry recycle process for recycling used slurry into makeup slurry of a consistent average particle size, where used slurry is processed by a separator into an abrasive-rich component containing relatively larger heavier particles and a kerf-rich component containing relatively smaller lighter particles, as compared to the mixture entering the separator. The process would include the monitoring of particle concentration of at least one component of slurry, and the adjusting of the separating force and dwell time of the separator in response to changes in particle concentration.

The process may include continuous or controlled recirculation of either or both slurry component outputs from the separator for mixing with more used slurry and reflowing of the mixture through the separator. There may be multiple stages of separating occurring in parallel or series, each with or without a recirculation loop, to provide the optimal discrimination and control of particle size and type going into the makeup slurry.

As another additional example, the slurry recycle process may be operated by or with a computer control system with suitable sensors and transducers for receiving data on particle concentration and other variables of slurry components, sending control signals for adjusting system settings and adding appropriate materials in response to changes in particle concentration.

As another example the systems and process described herein may be partially or fully integrated with a free-abrasive machine tool or tools as a complete method for free-abrasive machining operations such as slicing wafers from ingots, either manually operated or configured with computer controls.

The objects and advantages of the invention may be further realized and attained by means of the instrumentalities and combinations particularly pointed out in the appended claims. Accordingly, the drawing and description are to be regarded as illustrative in nature, and not as restrictive.

What is claimed is:

1. A free-abrasive machining slurry recycle system for processing used slurry into makeup slurry of constant average particle size comprising:
   a pre-separator section where said used slurry from a free-abrasive machine tool is received and conditioned for further processing,
   a separator wherein said used slurry is reduced into an abrasive-rich component of slurry and a kerf-rich component of slurry, said abrasive-rich component containing relatively larger heavier particles and said kerf-rich component containing relatively smaller lighter particles,
   means for monitoring particle concentration of at least one said component of slurry,
   means for adjusting a separating force and dwell time of said separator in response to changes in said particle concentration,
   means for adding additional abrasive or carrier to said abrasive-rich component as required in response to said changes in particle concentration, said makeup slurry comprising the result to said abrasive-rich component of said means for adjusting and said means for adding,
   means for dispensing said makeup slurry to said free-abrasive machine tool, and
   means for removing said kerf-rich component from said system.

2. The free-abrasive machining slurry recycle system of claim 1, said system being configured for operating in a batch mode wherein said free-abrasive machine tool is fully discharged of said used slurry into said pre-separator section and is subsequently recharged with said makeup slurry from said means for dispensing, and being further configured for recirculation of one said component from said separator to said pre-separator section for mixing of said component with said spent slurry in response to changes in said particle concentration.

3. The free-abrasive machining slurry recycle system of claim 1, said system being configured for operating in a continuous flow mode wherein said free-abrasive machine tool is continuously discharging said used slurry into said pre-separator section and is continuously recharging with said makeup slurry from said means for dispensing, and being further configured for recirculation of one said component from said separator to said pre-separator section for mixing of said component with said spent slurry in response to changes in said particle concentration.

4. The free-abrasive machining slurry recycle system of claim 1, said separator being a centrifuge.

5. The free-abrasive machining slurry recycle system of claim 1, said separator being a wet cyclone.

6. The free-abrasive machining slurry recycle system of claim 1, said recycle system further comprising a computer control system configured for receiving inputs from said means for monitoring particle concentration and for sending control signals to said means for adjusting said separator and said means for adding abrasive or carrier.

7. The free-abrasive machining slurry recycle system of claim 1, said machine tool being a wire saw used for slicing ingots into wafers.

8. The free-abrasive machining slurry recycle system of claim 1, said pre-separator section configured for controlling temperature of said used slurry.

9. The free-abrasive machining slurry recycle system of claim 1, said machine tool being a plurality of machine tools.

10. The free-abrasive machining slurry recycle system of claim 1, said system configured for recirculation of said kerf-rich component from said separator to said pre-separator section for mixing with said spent slurry in response to said changes in particle concentration.

11. The free-abrasive machining slurry recycle system of claim 1, said system configured for recirculation of said abrasive-rich component from said separator to said pre-separator section for mixing with said spent slurry in response to said changes in particle concentration.

12. A free-abrasive machining slurry recycle process for processing used slurry into makeup slurry of a consistent average particle size comprising
   separating said used slurry with a separator into an abrasive-rich component of slurry and a kerf-rich component of slurry, said abrasive-rich component containing relatively larger heavier particles and said kerf-rich component containing relatively smaller lighter particles,
   monitoring particle concentration of at least one said component of slurry,
   adjusting a separating force and dwell time of said separator in response to changes in said particle concentration,
   adding additional abrasive or carrier to said abrasive-rich component as required in response to said changes in particle concentration, said makeup slurry comprising a result to said abrasive-rich component of said means for adjusting and said means for adding.

13. The free-abrasive machining slurry recycle process of claim 12, further comprising recirculating and mixing said abrasive-rich component of slurry output from said separator with more said used slurry and flowing the mixture thereof into said separator.

14. The free-abrasive machining slurry recycle process of claim 12, further comprising recirculating and mixing said kerf-rich component of slurry out from said separator with more said used slurry and flowing the mixture thereof into said separator.

15. The free-abrasive machining slurry recycle process of claim 12, wherein said separator is a centrifuge.

16. The free-abrasive machining slurry recycle process of claim 12, wherein said separator is a wet cyclone.

17. The free-abrasive machining slurry recycle process of claim 12, further comprising using a computer control system with suitable sensors and transducers for receiving data indicating said particle concentration of said components, and sending control signals for said adjusting and said adding in response to changes in said particle concentration.

18. The free-abrasive machining slurry recycle process of claim 12, used in conjunction with at least one wire saw used for slicing ingots into wafers.

19. The free-abrasive machining slurry recycle process of claim 18, said recycle process further comprising using a computer control system with suitable sensors and transducers for receiving data indicating said particle concentration of said components, and sending control signals for said adjusting and said adding in response to changes in said particle concentration.

* * * * *